US00PP20451P3

(12) United States Plant Patent
FitzGerald

(10) Patent No.: US PP20,451 P3
(45) Date of Patent: Nov. 3, 2009

(54) **VARIETY OF *PHORMIUM* PLANT NAMED 'FIT01'**

(50) Latin Name: *Phormium cookianum*
Varietal Denomination: FIT01

(76) Inventor: Pat FitzGerald, Oldtown, Storneyford, Co Kilkenny (IE)

( * ) Notice: Subject to any disclaimer, the term of this patent is extended or adjusted under 35 U.S.C. 154(b) by 134 days.

(21) Appl. No.: 11/820,264

(22) Filed: Jun. 19, 2007

(65) Prior Publication Data

US 2008/0320628 P1 Dec. 25, 2008

(51) Int. Cl.
*A01H 5/00* (2006.01)

(52) U.S. Cl. ..... Plt./263.1

(58) Field of Classification Search ..... None
See application file for complete search history.

*Primary Examiner*—Wendy C. Haas
(74) *Attorney, Agent, or Firm*—Fulwider Patton LLP

(57) ABSTRACT

A new and distinct cultivar of *Phormium cookianum* plant named 'FIT01' characterized by shiny, deep blackish purple leaves, a tall and wide growth habit with wide leaves, and a robust appearance in adverse conditions.

1 Drawing Sheet

Latin name of the genus and species: The Latin name of the genus and species of the novel variety disclosed herein is *Phormium cookianum.*

Variety denomination: The inventive variety of the *Phormium* disclosed herein has been given the variety denomination 'FIT01'.

BACKGROUND OF THE NEW PLANT

The present invention relates to a new and distinct cultivar of *Phormium* plant, botanically known as *Phormium cookianum,* and further known by the varietal name 'FIT01'. This new variety is also sold under the trade name Black Adder (Breeder's Ref. No. 'FIT01'). The new variety was created through tissue culture mutation in Enniscorthy, Ireland, from the variety *Phormium cookianum* 'Platts Black.' This variety was selected as a single plant from a number of different natural mutations in a tissue laboratory in March 2003. Five different mutations were isolated for possible development, from which the present invention was chosen for further multiplication production. In January 2005, the cultures of 'FIT01' were further multiplied and the first crop began to develop. The variety was grown in both pots and one large original plant remains in situ outdoors. All plants were grown in Kilkenny, Ireland. For purposes of this application, the plants were evaluated outdoors and indoors in a plastic green house.

Following selection of the plantlet, the cultivar was propagated by tissue culture of multiplication from auxiliary growing shoots in a laboratory in Enniscorthy, Ireland. Continued observation of future generations have confirmed that the distinguishing features of this new cultivar came true, remain stable and are retained through successive propagation.

The closest comparator to 'FIT01' known to applicant is *Phormium cookianum* 'Platts Black' (unpatented). The present cultivar is much more vigorous and resilient when compared with 'Platts Black', and remains a healthier plaint in more adverse conditions than 'Platts Black'.

SUMMARY OF THE INVENTION

Plants of the cultivar 'FIT01' have not been observed under all possible environmental and cultural conditions. The phenotype of the new cultivar may vary somewhat with variations in environment such as temperature, light intensity, length of day, irrigation amount and frequency, and/or fertilizer rate without, however, any variance in genotype.

The following traits have been repeatedly observed and are determined to be among the unique characteristics of 'FIT01'. These characteristics distinguish 'FIT01' as a new and distinct cultivar from its closest comparator *Phormium cookianum* 'Platts Black':

1. Leaves are deep blackish purple all year; and
2. The foliage is more glossy and wider than 'Platts Black'; and
3. The growth habit is taller than 'Platts Black' and the leaf is wider. For two year old specimens of 'FIT01' and 'Platts Black', the present cultivar demonstrated a 110 cm length leaf as compared with a 65 cm length for 'Platts Black' and the present cultivar had a 4.5 cm width leaf as compared with a 3 cm width for 'Platts Black'.

BRIEF DESCRIPTION OF THE DRAWINGS

The invention is depicted in the accompanying colored photographs in which.

Figure 1:
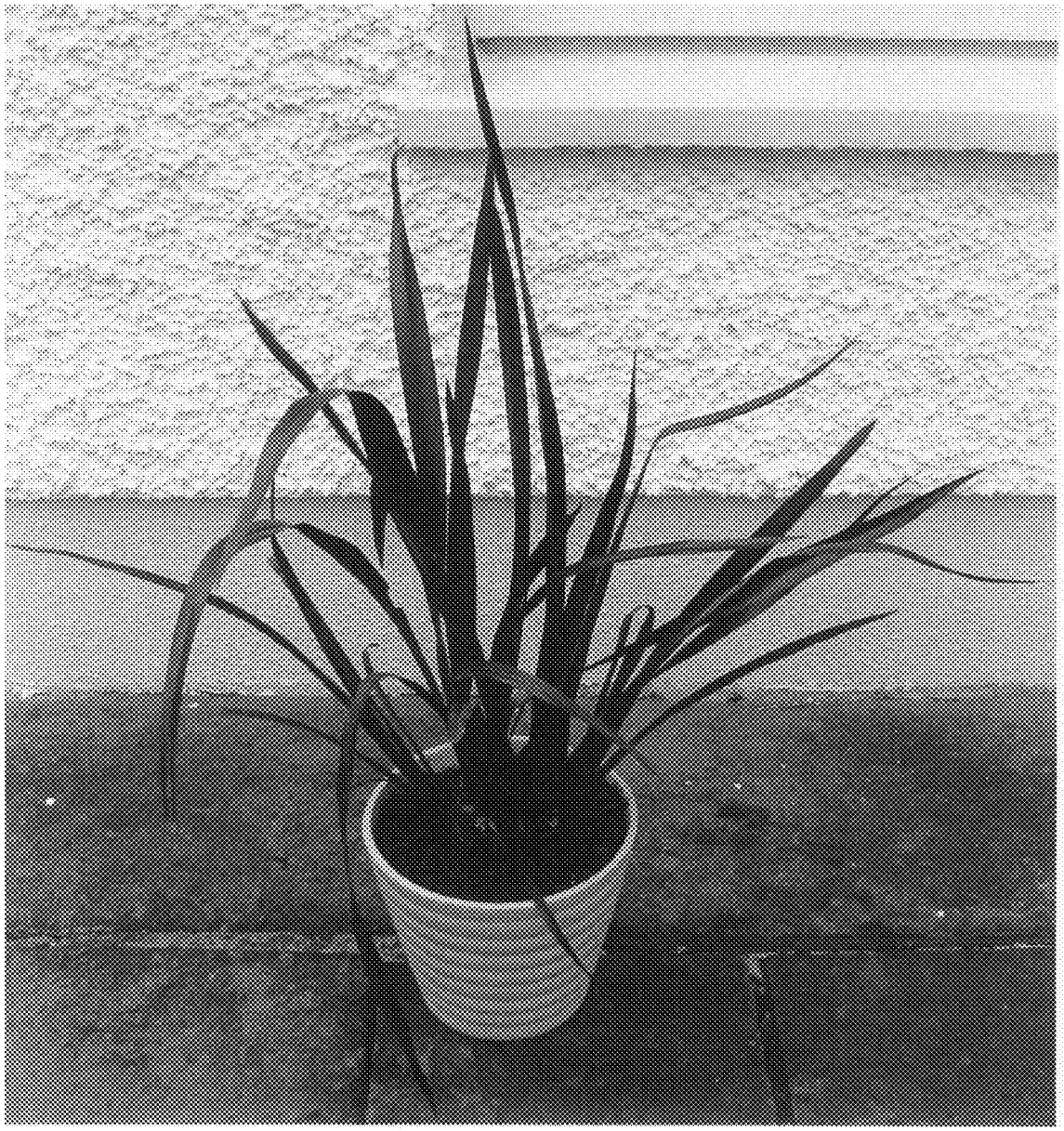
FIG. 1 shows a potted plant illustrating the characteristic foliage.

The photograph depicts the overall appearance of the new *Phormium,* showing the colors as true as it is reasonably possible to obtain in colored reproductions of this type. Colors in the photograph may differ slightly from the color values cited in the Detailed Botanical Description which more accurately describe the actual colors of the new *Phormium.*

DETAILED BOTANICAL DESCRIPTION OF THE NEW PLANT

The following detailed description sets forth characteristics of the new cultivar. The data which defines each characteristic was collected from reproductions of the plant grown in a plastic greenhouse and outdoors.

In the following table of plant characteristics, color references are made to The Royal Horticultural Society of London Colour Chart, 1995 Edition (hereafter "R.H.S.").

THE PLANT

Classification:

*Botanical.*—*Phormium cookianum.*

*Varietal name.*—'FIT01'.

*Parentage.*—Tissue Culture Mutation of *Phormium cookianum* 'Platts Black'.

*Asexual propagation.*—Tissue culture mutation.

Form:

*Plant growth type.*—Upright with drooping tips.

*Mean plant height.*—1.5 M.

*Mean plant width.*—1.5 M.

Leaves:

*Leaf color.*—Young Upper — Gray-purple to brown; in between N186C and 200B, but slightly darker (RHS) Young Under — Gray-purple to brown, in between N186C and 200A, but slightly darker (RHS) Mature Upper — Brown, 200A but slightly darker (RHS) Mature Under — Brown, 200A (RHS).

*Vein color.*—Upper — Gray-Orange 177A (RHS) Under — Brown 200A (RHS) Leaf Shape — Wide lanceolate strap-like leaves Leaf Length — 73 cm (1 year old plant) Leaf Width — 3.4 cm (1 year old plant) Tip Shape — Acute Base Shape — Acuminate Margin — Entire.

*Leaf texture* (*upper*).—Shiny, waxy surface.

*Venation pattern.*—Parallel.

Flower: Flower development has not been observed on plants of the new *Phormium.*

Lasting quality: The *Phormium* is outstanding in wind and sun, as the foliage remains shiny and vibrant throughout the year. Providing the plant is not exposed to temperatures below −7° C., the plant will remain stable and colorful all year round.

Disease resistance: No known diseases have affected this plant to date.

GENERAL CHARACTERISTICS

'FIT01' is primarily distinguished from other cultivars of *Phormium* genus by its deep blackish purple leaves having a glossy shine. 'FIT01' is an upright forming plant with a wide and tall growth habit.

What is claimed is:

1. A new and distinct *Phormium cookianum* plant named 'FIT01' substantially as illustrated and described.

* * * * *